United States Patent [19]

Shulman et al.

[11] Patent Number: 5,097,820
[45] Date of Patent: Mar. 24, 1992

[54] ARTICULATING MOUTH-PROP DEVICE FOR USE IN THE DIAGNOSIS AND/OR TREATMENT OF PATIENTS SUFFERING FROM TRISMUS OR OTHER MEDICAL OR DENTAL PROBLEMS OR FOR OTHER PURPOSES

[76] Inventors: David H. Shulman, 2 Hickory Hill Rd., Hunt Valley, Md. 21030; Barry R. Berman, 2413 Velvet Ridge Dr., Owings Mills, Md. 21117; Paul Varga, 213 W. Philadelphia Ave., Salisbury, Md. 21801

[21] Appl. No.: 600,601

[22] Filed: Oct. 19, 1990

Related U.S. Application Data

[62] Division of Ser. No. 344,068, Apr. 25, 1989, Pat. No. 4,991,566.

[51] Int. Cl.⁵ .................................................. A61B 1/32
[52] U.S. Cl. ......................................... 128/17; 128/20
[58] Field of Search ..................................... 128/15–20, 128/857, 859–862; 433/140

[56] References Cited

U.S. PATENT DOCUMENTS

| | | | |
|---|---|---|---|
| 742,698 | 10/1903 | Mason | 128/17 |
| 815,907 | 3/1906 | Davis | 128/17 |
| 902,993 | 11/1908 | McIntosh | 128/17 |
| 1,025,265 | 5/1912 | Grindle | 128/17 |
| 1,229,595 | 6/1917 | Brul | 433/140 |
| 2,708,931 | 5/1955 | Freedland | 128/861 |
| 3,616,792 | 11/1971 | Pleet | 128/16 |
| 4,700,695 | 10/1987 | Davis et al. | 128/17 |
| 4,991,566 | 12/1991 | Shulman et al. | 128/17 |

FOREIGN PATENT DOCUMENTS

| 17220 | of 1900 | United Kingdom | 128/17 |
|---|---|---|---|
| 5986 | of 1907 | United Kingdom | 128/17 |

*Primary Examiner*—Stephen C. Pellegrino
*Assistant Examiner*—Ralph A. Lewis
*Attorney, Agent, or Firm*—Leonard Bloom

[57] ABSTRACT

A device for dilating and propping open a patient's jaws. The device includes a pair of outwardly-extending upper arms and a pair of outwardly extending lower arms. Each of the arms has a respective distal end which as a pad pivotally mounted thereon which contacts the patient's jaws during use thereof, and a respective proximal end which is pivotably secured to the housing. Means is provided for pivoting the distal ends of the upper arms towards and away from the distal end of the lower arms such that the distal ends move substantially arcuately between the open and closed positions. A worm and worm wheel arrangement is provided for pivoting the arms, such that the spacing therebetween is infinitely variable.

6 Claims, 6 Drawing Sheets

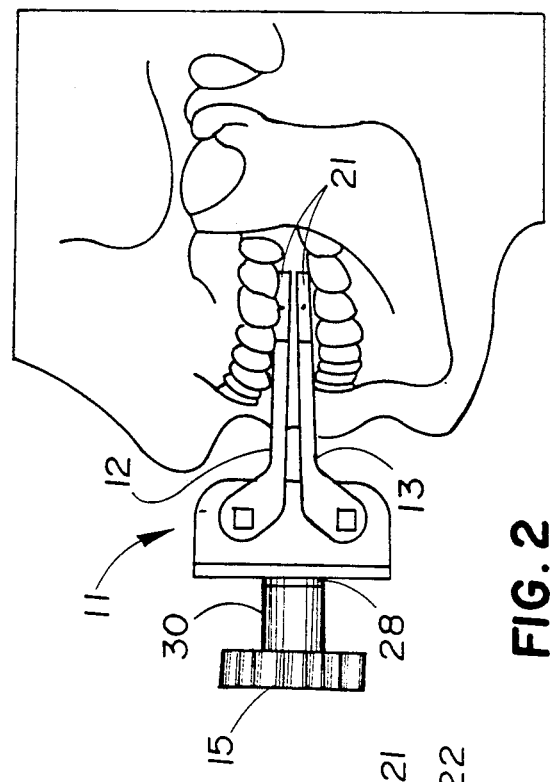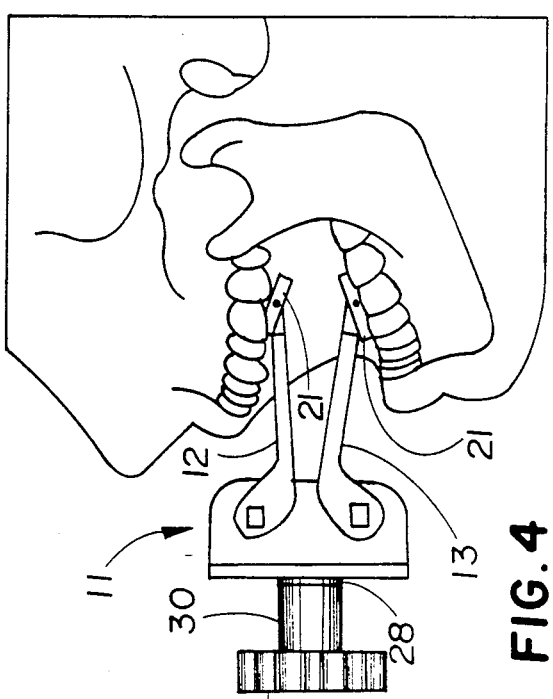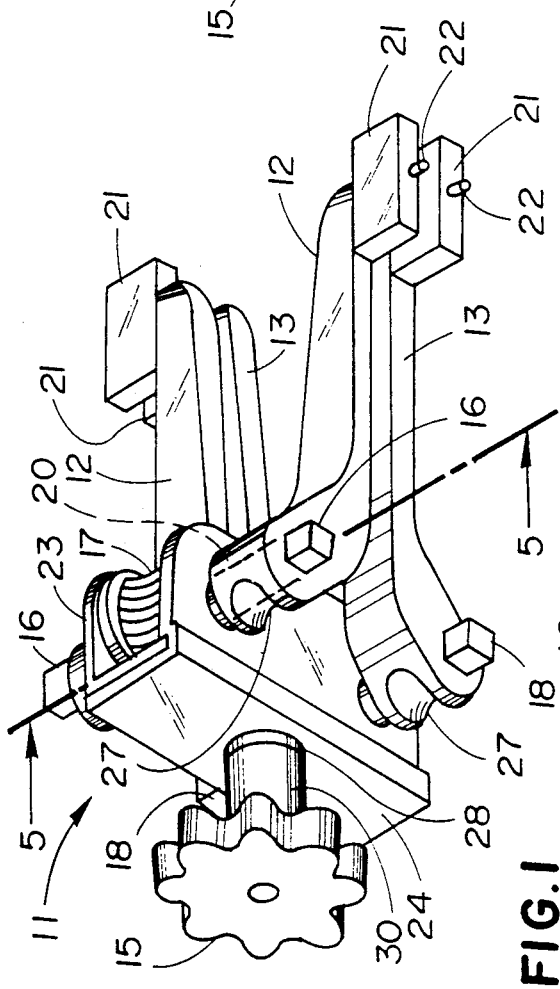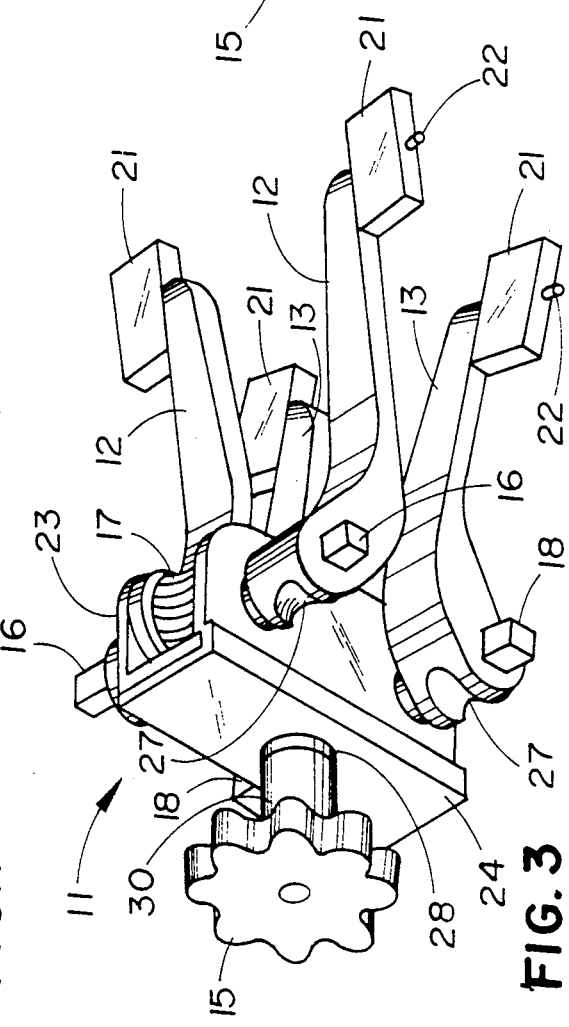

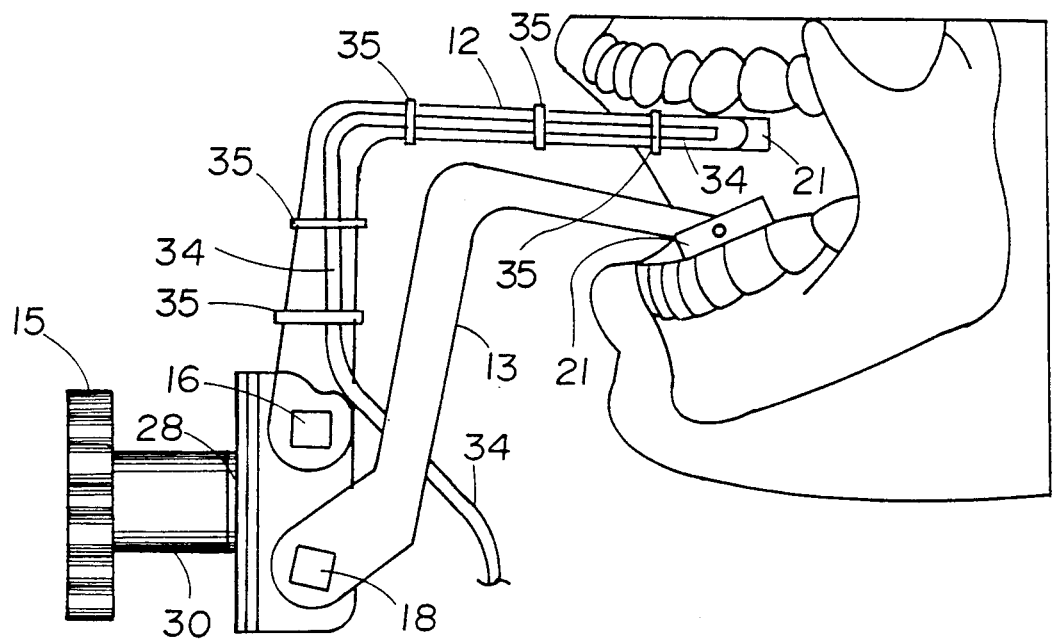
FIG.10
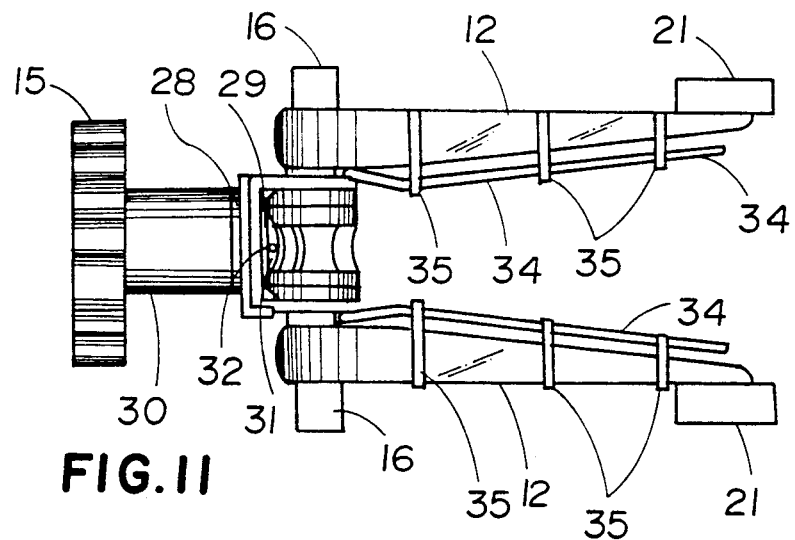
FIG.11
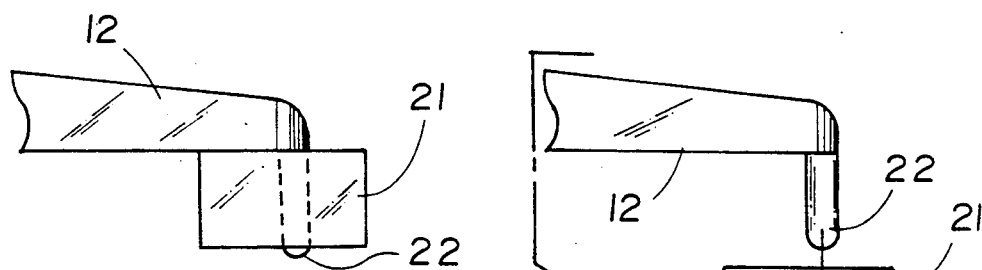
FIG.12
FIG.13

5,097,820

ARTICULATING MOUTH-PROP DEVICE FOR USE IN THE DIAGNOSIS AND/OR TREATMENT OF PATIENTS SUFFERING FROM TRISMUS OR OTHER MEDICAL OR DENTAL PROBLEMS OR FOR OTHER PURPOSES

This application is a division of application Ser. No. 344,068, filed Apr. 25, 1989 now U.S. Pat. No. 4,991,566.

FIELD OF THE INVENTION

The present invention relates to devices for dilating and propping open the jaws of a patient and, in particular to a device for opening the mouth which is afflicted with trismus.

BACKGROUND OF THE INVENTION

Trismus is reduced mouth opening that results from trauma, infection, a sequaele of surgery, muscle spasm of the muscles of mastication, rheumatoid and osteoarthritis, tumors, tendonitis or internal derangment of the jaw joint, etc. A person afflicted with trismus is not able to fully open their lower jaw. This is problematic in that, often, access to the interior of the afflicted person's mouth and throat is necessary to effectively treat the cause of the affliction. Approximately 75,000 to 100,000 person in the United States require treatment for this ailment annually.

Additionally, there are other occasions, such as during an examination or any procedure performed with or without general or local anesthesia, when the patient's mouth must be propped open.

There are several devices of which I am aware which are provided for dilating and/or for propping open a human mouth. The Heister mouth prop consists of a pair of arms which can be adjusted to an open position by a hand adjustable threaded screw. The ends of the arms are serrated to grip the teeth or a sleeve which can be placed over the ends. The Maunder screw jaw spreader is a spiral plug which is inserted between the patient's teeth and hand adjusted to prop open the mouth. Also, there are several mouth-gag devices of the hemostat variety such as the Hu-Friedy Molt, Ace Molt, Ace Doyen Collin Molt, Ace Doyen Jansen Molt and Ace Denhardt Mouth Gags. In addition, the Dingman Mouth Gag is a frame with coiled springs, tongue depressors, cheek retractors and movable tooth hooks which is positioned in front of the mouth. The McIvor Mouth Gag is a substantially triangular frame with an attached adjustable tongue depressor. The Davis-Boyle Mouth Gag is a reverse "C" shaped frame with an adjustable tongue depressor. In U.S. Pat. No. 2,061,936 issued to Engelfried, a mouth prop is disclosed that is inserted between a patient's teeth. This device includes a threaded bolt that carries a pair of bars thereon that, carrying tooth engagement means thereon, are linearly movable to prop a mouth open. In U.S. Pat. No. 2,182,390 issued to Reardon, a surgical device is disclosed for propping open the mouth of a patient, so as to permit access to and illumination of the area in back of the nose and above the palate.

While being useful for their purpose, both of these patented devices have particular drawbacks, especially where the patient is afflicted with trismus. In particular, in both devices, as well as in all other devices of which I am aware, the jaw supporting portions move away from and towards one another in a straight linear fashion. Unfortunately, the mandible does not move in such a linear fashion. The jaw joint is a ginglimoarthroidial joint and, as such, moves in a sliding pivotal articulation (where the lower jaw joins the skull), such that the lower jaw pivotally moves away from and towards the skull in a substantially arcuate path. Thus, if the devices disclosed in Engelfried and Reardon would be utilized to open a jaw afflicted with trismus, the tooth engaging portions thereof, while moving linearly, would slip or ride over the teeth of the jaw, which moves arcuately. Such an arrangement can result in breaking and/or other damage occurring to the teeth and/or jaw of the patient.

Thus, it can be seen that there remains a need for a device for dilating and/or propping open a jaw which has tooth (or jaw) engaging portions that pivot outwardly from and towards one another, moving in a substantially arcuate path.

SUMMARY OF THE INVENTION

Accordingly, it is a primary object of the present invention to provide a device for dilating, and/or propping open a patient's jaw, which has tooth and/or jaw engaging portions that move in a substantially arcuate path, being pivotably movable outwardly from and towards one another.

It is another object of the present invention to provide such a device that is particularly applicable for use on a patient afflicted with trismus and which will not damage the patient's teeth and/or jaw.

It is a further object of the present invention to provide such a device wherein, by use of a single control, the teeth engaging portions thereof may be simultaneously moved, so as to be infinitely variable.

In accordance with the teachings of the present invention, there is disclosed a device for dilating and propping open a jaw. This device includes a housing. A pair of parallel upper arms are provided. Also, there are a pair of parallel lower arms. Each of the upper arms is positioned substantially above a respective lower arm. Each of the arms has a distal end for contacting the jaws and a proximal end being pivotably carried by the housing for pivotal movement upwardly and downwardly between open and closed positions. In this fashion, in the open position, each of the distal ends of the upper arms are spaced apart from the distal end of the lower arm above which the upper arm is positioned, and, in the closed position, each of the distal ends of the lower arms are substantially adjacent to the distal end of the lower arm above which the upper arm is positioned. Means is provided for pivoting the upper and the lower arms simultaneously towards one another into the closed position for allowing the jaw to naturally close and for pivoting the upper and the lower arms simultaneously away from one another into the open position for dilating and propping open the jaw. In this fashion, the distal ends of the arms move substantially arcuately. Also, the spacing between the upper and lower arms is infinitely variable.

In further accordance with the teachings of the present invention, there is disclosed a device for dilating, and propping open a dilated jaw. This device includes a housing. A worm having a longitudinal axis is provided. The worm is positioned for rotational movement about the longitudinal axis thereof in a first opening direction and in a second opposite closing direction. An upper worm wheel shaft is provided which has a longitudinal axis and a pair of opposite ends. The upper worm wheel shaft is rotationally carried by the housing for rotational movement about the longitudinal axis in a first opening direction and a second, opposite closing direction.

A lower worm wheel shaft is provided which has a longitudinal axis and a pair of opposite ends. The lower worm wheel shaft is rotationally carried by the housing for rotational movement about the longitudinal axis in a first opening direction and a second, opposite closing direction, the lower worm wheel shaft is situated below and parallel to the upper worm wheel shaft.

An upper worm wheel is rotationally carried on the upper worm wheel shaft between the opposite ends thereof for rotational movement about the longitudinal axis of the upper worm wheel shaft concommittantly therewith in the first opening and second closing directions. A lower worm wheel is rotationally carried on the lower worm wheel shaft between the opposite ends thereof for rotational movement about the longitudinal axis of the lower worm wheel shaft concommittantly therewith in the first opening and second closing directions. The worm further is cooperatively associated with each of the worm wheels. In this manner, each of the worm wheels moves simultaneously in the respective first opening and the second closing directions thereof in response to the rotational movement of the worm in, respectively, the first opening direction and the second closing directions. A pair of parallel outwardly-extending upper arms are provided. Each of the upper arms is associated with a respective opposite end of the upper worm wheel shaft at respective pivot points for pivotal movement thereabout. This movement is in a first upward opening direction and in a second downward closing direction in response to the rotational movement of the upper worm wheel and the upper worm wheel shaft in respectively, the first opening and second closing directions. A pair of parallel outwardly-extending lower arms are also provided. Each of the lower arms is joined to a respective opposite end of the lower worm wheel shaft at respective pivot points for pivotal movement thereabout. This movement is also in a first opening downward direction and in a second closing upward direction in response to the rotational movement of the lower worm wheel and the lower worm wheel shaft in, respectively, the first opening and second closing directions. Finally, each of the upper and lower arms includes respective distal ends which contact the patient's jaw during the dilation and propping open thereof. In this manner the pivotal movement of the upper and lower arms moves the distal ends thereof substantially arcuately for moving the lower jaw therewith.

Each of the distal ends of each of the upper and the lower arms has a respective pad carried thereon, whereby a cushion between the distal ends of the arms and the jaw is provided. A means is provided for removably securing each pad on the distal end of a respective arm.

The distal end of each upper arm has a peg formed thereon, extending inwardly or outwardly therefrom. The distal end of each lower arm also has a peg formed thereon extending inwardly or outwardly therefrom. Combinations of inwardly and outwardly extending pegs may be selected on the upper and lower arms by appropriate mounting of the interchangeable arms.

Each pad has an opening formed therein for snugly receiving one of the pegs therein. A respective pad may be removably received on the distal end of each arm. The pads may be selectively removed from the arms, so that pads of varying thicknesses, sizes and shapes may be utilized. Each pad may pivot about the shaft during arcuate upward and downward movement of the upper and lower arms.

An upper shaft and a lower shaft are rotationally carried by the housing. Each shaft has a longitudinal axis extending beyond the first side and second side of the housing. Means are provided for slidably mounting the proximal ends of the upper arms to the upper shaft and the proximal ends of the lower arms on the lower shaft, respectively on the first side and the second side of the housing. The proximal ends of each arm can be independently adjusted laterally to any desired position on the respective shafts so that the distal ends of the upper arms and the lower arms conform to the jaw. The arms are interchangeable and may be mounted on either the upper or lower shaft. A groove is provided in the proximal end of the arm such that it can be digitally slidably adjusted to any desired position on the shaft.

In this invention, the term jaw may apply to either the upper jaw (maxilla) or lower jaw (mandible). Also, the skull (maxilla) is a fixed object and the lower jaw (mandible) is movable. The mouth prop device of this invention operates to open the jaws to accurately duplicate the natural arc of opening. The pads which are on the distal ends of the arms and which contact the teeth or gums, pivot on the arms during arcuate opening and/or closing of the arms so that there is no slippage of the device and, consequently, no injury to the patient.

These and other objects of the present invention will become apparent from a reading of the following specification, taken in conjunction with the enclosed drawings.

BRIEF DESCRIPTION OF THE DRAWINGS

FIG. 1 is a perspective view of the device in its closed position.

FIG. 2 illustrates the device in a closed position in the oral cavity resting against the upper and lower jaws.

FIG. 3 is a perspective view of the device in its open position.

FIG. 4 illustrates the device in an open position in the oral cavity resting against the upper and lower jaws.

FIG. 10 illustrates the device of FIG. 9 having a cable and light source attached to the inner side of the upper arm.

FIG. 11 is a top view of the device of FIG. 9 showing the cable and light source attached to the inner side of the upper arm.

FIG. 12 is an enlarged view of the pad mounted on the pad shafts.

FIG. 13 is an enlarged view in partial cross section of the pad removed from the pad shaft.

DESCRIPTION OF THE PREFERRED EMBODIMENTS

Figure 5:
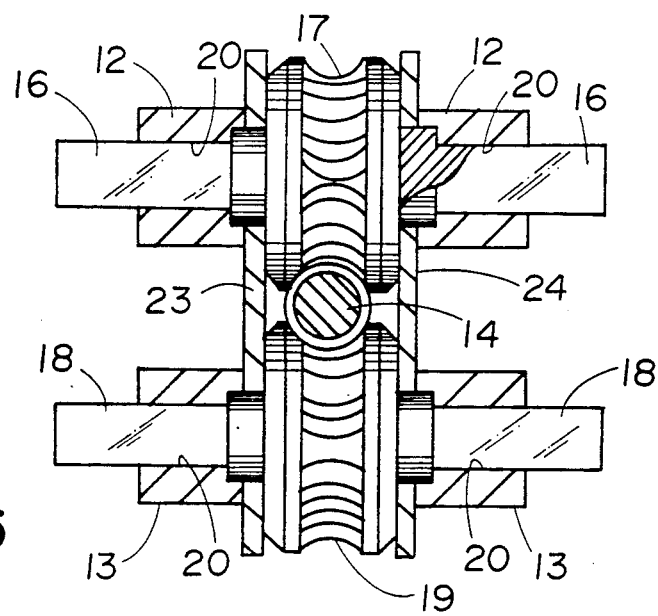
FIG. 5 is a cross-section taken across the lines 5—5 of FIG. 1 showing the worm wheel and worm wheel shaft.

With reference now to the drawings, the device includes a housing 11 that is generally in the form of two "L" shaped portions nested to form a U-shaped bracket. However, it is to be understood that any suitably shaped housing or support may be utilized.

With respect to FIG. 1, a pair of parallel upper dilating arms 12 are carried by the upper worm wheel shaft 16. These upper arms 12 are generally outwardly-extending. Upper arms 12 are pivotably carried by the upper worm wheel shaft 16 for substantially vertical upward and downward movement in a first upward opening direction and in a second downward closing direction.

A pair of parallel lower dilating arms 13 are also carried by the lower worm wheel shaft 18. These lower arms 13 are also generally outwardly-extending, each further being positioned substantially below and vertically parallel to a respective upper arm 12. Positioned thusly, the lower arms 13 are pivotably carried by the lower worm wheel shaft 18 for substantially vertical upward and downward movement in a first downward opening direction and in a second upward closing direction. One arm may be articulated relative to the other arm.

Figure 7:
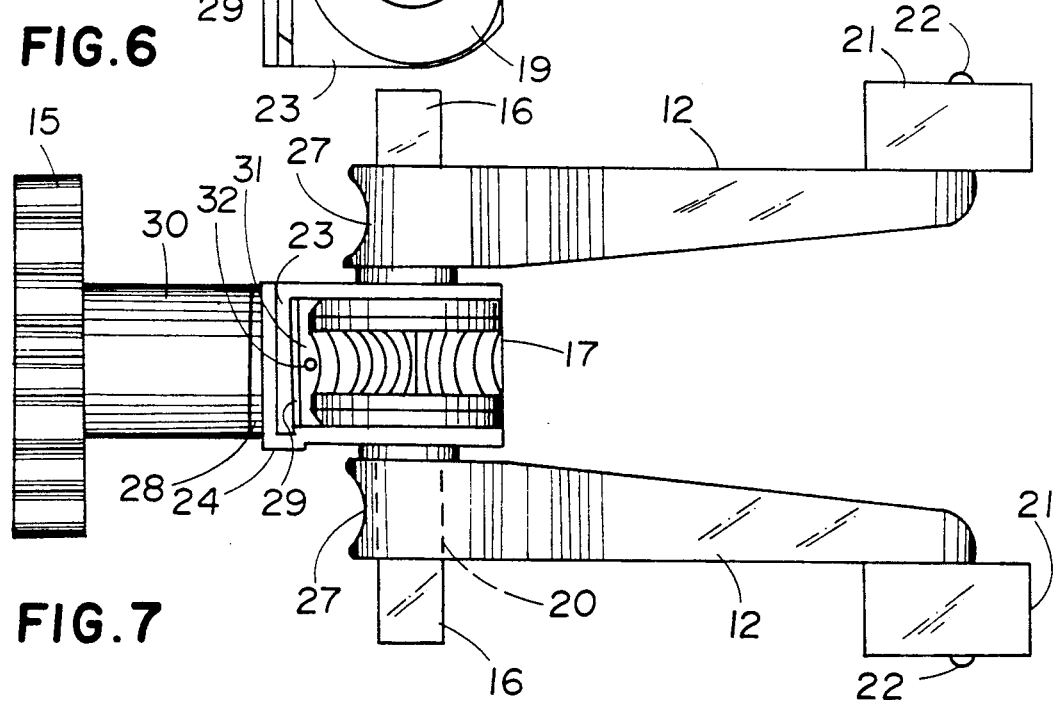
FIG. 7 is a top view showing the upper worm wheel, the upper arm and the knob.

With respect to FIGS. 1, 3 and 7, each of the arms 12 and 13 have respective proximal and distal ends. The distal ends contact and/or carry means thereon which contact a respective portion of the jaw during the opening and propping open operations. The proximal ends of each of the arms 12 and 13 are, as shall be discussed in detail below, pivotably carried by the worm wheel shafts 16 and 18 for providing pivotal movement of the arms 12 and 13 between respective open and closed positions. In the open position, the distal ends of the upper arms 12 are spaced apart from the distal end of the lower arm 13 above which it is positioned. In the closed positions, the distal ends of the upper arms 12 are substantially adjacent to the distal end of the lower arm 13 above which it is positioned.

The above-mentioned pivotal movement of each arm 12 and 13 about the respective pivot points thereof moves the distal ends of the arms 12 and 13 in a substantially arcuate path. This movement imitates the pivotal movement made by the jaw during the opening and closing thereof. This permits the device to smoothly open the user's mouth without substantial pressure being exerted thereon by the distal ends of the arms. Thus the distal ends of the arms 12 and 13 do not slide or "ride" over teeth during use thereof nor does it place undue pressure on the teeth of the jaw being opened thereby.

It is preferred that each of the arms 12 and 13 have a respective curvature formed therein between the proximal and distal ends thereof. This curvature also aids the arms 12 and 13 in moving the distal ends in the substantially arcuate path for simulating the movement of the jaw. In this regard, the lower arms 13 are curved downwardly and the upper arms 12 are curved upwardly. In this fashion, in the closed position, the distal ends of the arms 12 and 13 are substantially parallel to one another.

As shown in FIGS. 2 and 4, means is also provided for pivoting the upper and lower arms 12 and 13 simultaneously either towards one another and into the closed position when the mouth is to be closed or away from one another and into the open position for opening (dilating) the jaw. In addition to pivotably moving the distal ends of the arms in a substantially arcuate path, this means further permits the arms 12 and 13 to be adjusted, so that the spacing therebetween is infinitely variable. Each arm has a groove 27 on the proximal end for digitally adjusting the lateral position of the respective arm.

Figure 6:
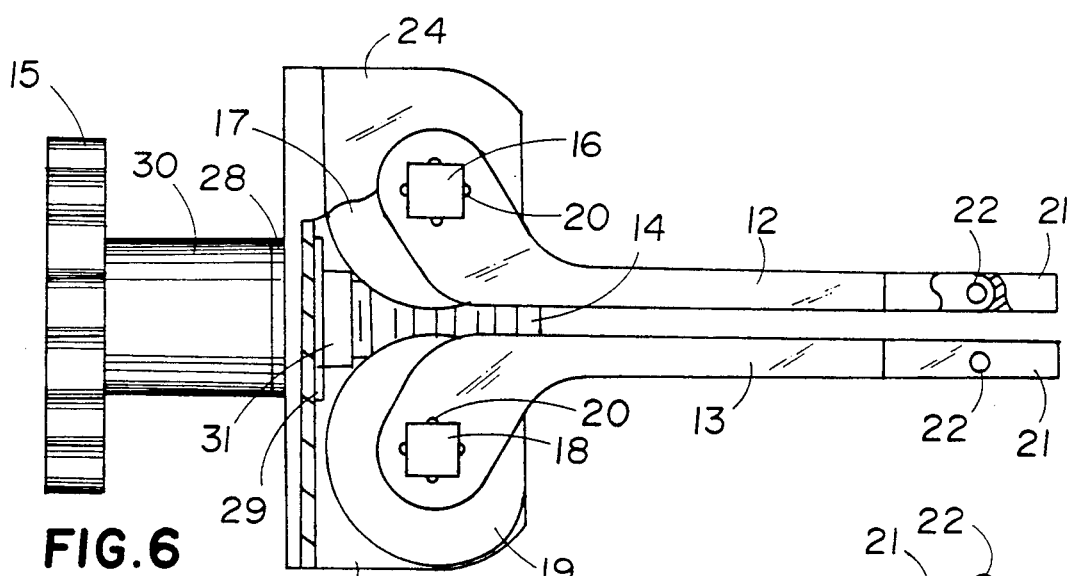
FIG. 6 is a side elevation with a partial cross section of the second outer "L" shaped section showing the upper and lower worm wheels, the worm and knob.

With respect to FIGS. 5-7, the means for pivoting the upper and lower arms 12 and 13, respectively, includes a worm 14. Worm 14 has a longitudinal axis that is oriented substantially parallel to the distal ends of the arms 12 and 13, when the arms 12 and 13 are in the closed position. Worm 14 is at least partially housed in and is rotatably carried by the housing for rotational movement about the longitudinal axis in a first opening (counterclockwise) direction and in a second opposite closing (clockwise) direction.

Preferably, the worm 14 is driven by (associated with) a manually-manipulatable member such as a knob or handle 15. Knob 15 includes a portion which facilitates gripping by the user during operation thereof. The knob 15 is carried by the housing 11 for rotational movement in the same identical first and second directions as the worm 14. The worm 14 has one end that is, preferably, secured to the knob 15, such that the longitudinal axis of the worm 14 intersects the centerpoint of the knob 15. In this fashion, the knob 15 and the worm 14 are made integral. This permits manual rotation of the knob 15 in the first opening and second closing directions to drive the worm 14 concommittantly for rotational movement therewith. The knob further has a means which may be used to indicate rotation through a full revolution. A complete revolution of the knob represents approximately 10 mm of movement between the distal ends of the arms. Users of the device should know the size of the opening for proper treatment. Furthermore, the first and second arms are infinitely adjustable upon movement of the knob to obtain the desired opening of the jaws.

An upper worm wheel shaft 16 is carried by the housing 11 for rotational movement about the longitudinal axis thereof in a first opening direction and in a second, opposite closing direction. This upper worm wheel shaft 16 is located above the worm 14 and is oriented, such that the longitudinal axis thereof is perpendicular to the longitudinal axis of the worm 14. The upper worm wheel shaft 16 is mounted in the housing with the (pair of) opposite ends (laterally-extending portions) extending laterally-outwardly therefrom.

A proximal end of each of the upper arms 12 is connected to a respective opposite end of the upper worm wheel shaft 16, so that there are two upper arms 12 thereon. In this fashion, the rotational movement of the upper worm wheel shaft 16 in the first opening direction concommittantly pivots the upper arms 12 therewith in the first upward opening direction. Further, the rotational movement of the upper worm wheel shaft 16 in the second closing direction concommittantly pivots the upper arms 12 therewith in the second downward closing direction.

Preferably, as shown in FIG. 5, the proximal end of each of the upper arms 12 is connected to a respective opposite end of the upper worm wheel shaft 16 by being keyed thereto. In this respect, the opposite ends (the laterally-extending portions) of the shaft 16 have a square, or other polygonal cross-section. The proximal ends of each of the upper arms 12 has an aperture 20 formed, therein (at a pivot point) that is likewise of a square or polygonal cross-section. This aperture 20 is also sized so that the opposite ends of the shaft 16 may be received therethrough, such that the arms 12 are keyed to the respective opposite ends of the shaft 16 at the pivot point for pivotal movement of the upper arm 12 thereabout.

An upper worm wheel (the one of the worm wheels) 17 is mounted on and carried by the shaft 16 for concommittant rotational movement therewith about the longitudinal axis of the shaft 16 in first opening and second opposite closing directions. It is noted that these are the same rotational first opening and second closing directions as described above relative to the shaft 16. The upper worm wheel 17 is thus rotatably carried by the housing above the worm 14 and is cooperatively associated therewith in a manner that is well known to those skilled in the art. In this fashion, the rotational movement of the worm 14 in the first opening direction drives the upper worm wheel 17 (and the upper worm wheel shaft 16) therewith in their respective first opening directions. Further, the rotational movement of the worm 14 in the second closing direction drives the upper worm wheel 17 (and the upper worm wheel shaft 16) therewith in their respective second closing directions.

A lower worm wheel shaft 18 is carried by the housing 11 for rotational movement about the longitudinal axis thereof in a first opening and a second, opposite closing direction. The lower worm wheel shaft 18 is located below the worm 14 and is oriented, such that the longitudinal axis thereof is substantially parallel to the longitudinal axis of the upper worm wheel shaft 16 and perpendicular to the longitudinal axis of the worm 14. The lower worm wheel shaft 18 is mounted in the housing with the (pair of) opposite ends (laterally-extending portions) extending laterally-outwardly therefrom.

A proximal end of each of the lower arms 13 is connected to a respective opposite end of the lower worm wheel shaft 18, so that there are two lower arms 13 thereon. In this fashion, the rotational movement of the lower worm wheel shaft 18 in the first open direction concommittantly pivots the lower arms 13 therewith in the first downward opening direction. Further, the rotational movement of the lower worm wheel shaft 18 in the second closing direction concommittantly pivots the lower arms 13 therewith in the second upward closing direction.

Preferably, as with the upper arms 12, the proximal end of each of the lower arms 13 is connected to a respective opposite end of the lower worm wheel shaft 18 by being keyed thereto. In this respect, the opposite ends (the laterally-extending portions) of the shaft 18 have a square, or other polygonal cross-section. The proximal ends of each of the lower arms 13 has an aperture 20 formed therein (at a pivot point) that is of a likewise square or polygonal cross-section. This aperture 20 is also sized, so that the opposite ends of the shaft 18 may be received therethrough, such that the arms 13 are keyed to the respective opposite ends of the shaft 18 at the pivot point for pivotal movement of the lower arms 13 thereabout. The arms 12, 13 are interchangeable and either end of the upper shaft 16 or the lower shaft 18 may be received in the aperture 20 on the proximal end of any arm. The arms 12, 13 may be of differing lengths to accommodate larger or smaller jaws or to permit use of the device with patients having irregular jaw structure.

Figure 8:
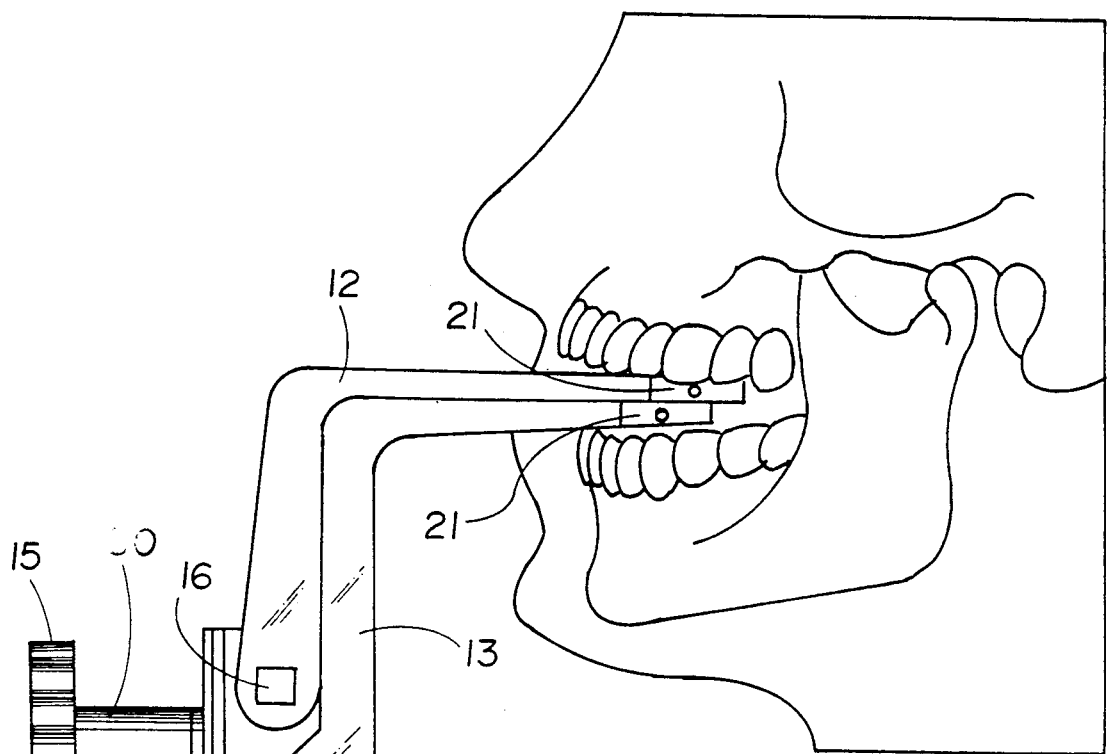
FIG. 8 illustrates arms of extended offset length and curvature on the device in a closed position in the oral cavity resting against the upper and lower jaws showing disposition of the housing beneath the lips.
Figure 9:
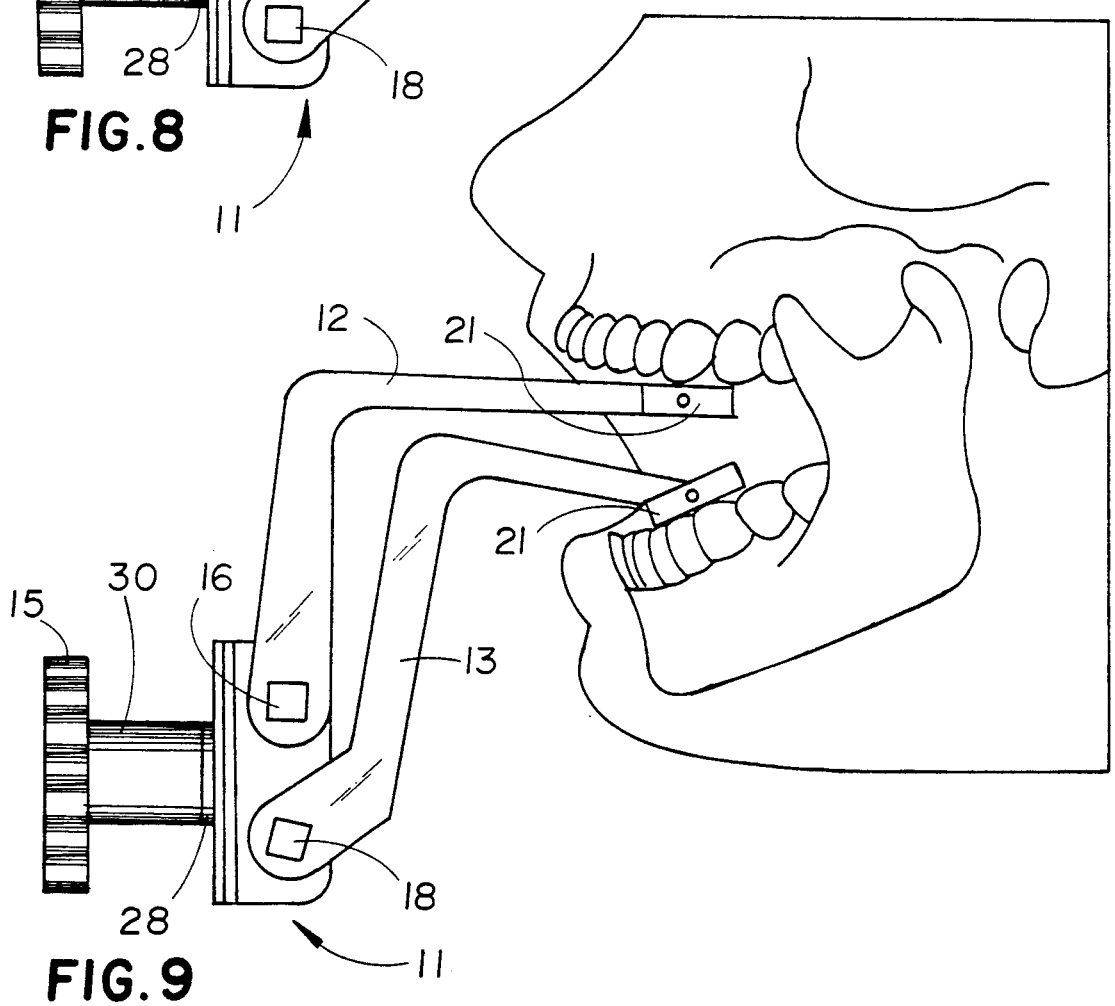
FIG. 9 illustrates the device of FIG. 8 in an open position in the oral cavity resting against the upper and lower jaws.

Further, as in FIGS. 8 and 9, the arms 12, 13 may be configured such that when the device is assembled, the housing 11 is disposed beneath the lips of the patient. This arrangement permits ease of access to the mouth, jaw, throat or beyond by health specialists. Also, as shown in FIGS. 10 and 11, in this configuration, a light source 34 may be attached to the upper arms 12 to illuminate the oral cavity and throat. The light source 34 may be a fiber optic type but any type known to those familiar with the art may be used. The fiber optic or power cord is shown attached to the inner side of the upper arms by a clip 35 but other means of attachment may be employed. In addition, endoscopic tubes may be attached to the device in a similar manner to allow deeper examination of the pharnyx, digestive system and/or bronchial passages.

A lower worm wheel (the other of the worm wheels) 19 is integral with, or mounted on, and is carried by the shaft 18 for concommittant rotational movement therewith about the longitudinal axis of the shaft 18 in the first opening and second opposite closing directions. It is noted that these are the same rotational first opening and second closing directions, as described above relative to the shaft 18. The lower worm wheel 19 is thus rotatably carried by the housing below the worm 14 (and below the upper worm wheel 17) and is cooperatively associated therewith in a manner that is well known to those skilled in the art. In this fashion, the rotational movement of the worm 14 in the first opening direction drives the lower worm wheel 19 (and the lower worm wheel shaft 18) therewith in their respective opening directions. Further, the rotational movement of the worm 14 in the second closing direction drives the lower worm wheel 19 (and the lower worm wheel shaft 18) therewith in their respective second closing directions.

It is also noted that the upper worm wheel 17 is opposite to the lower worm wheel 19. That is to say, the rotation of the upper worm wheel 17 in its first opening direction, is opposite to the rotation of the lower worm wheel 19 when it is rotating in its first opening direction. Also, the rotation of the upper worm wheel 17 in its second closing direction, is opposite to the rotation of the lower worm wheel 19 when it is rotating in its second closing direction. In this fashion, the arms 12 and 13 are able to be simultaneously moved towards and away from one another during use of the device 10.

In an alternate embodiment, the upper worm wheel 17 or the lower worm wheel 19 may be omitted so that the worm 14 drives only one worm wheel and, consequently, the arm or arms associated with the respective worm wheel. Thus, rotation of the knob 15 would produce movement of one arm or pair of arms, either upper 12 or lower 13, which would move pivotably upwardly and downwardly with respect to the other, substantially stationary, arm or pairs of arms.

Finally a cushioning or pad 21 is either carried on or by each respective distal end of the arms 12 and 13, such that a cushion is provided between the device and the jaw/tooth of an afflicted individual. Preferably, the pad is fabricated or molded from a substantially rigid, pliable plastic material.

Preferably, as shown in FIG. 12, the pads 21, are each carried by a respective pad shaft 22. A respective pad shaft 22 is provided for each arm 12 and 13. Shaft 22 has pair of ends and a longitudinal axis. One of the ends of each pad shaft 22 is carried by the distal end of a respective arm 12 or 13. The other of the said ends of the shaft 22 has a respective pad 21 carried thereon for concommittant pivotal movement with the pad shaft 22. In this fashion, each of the pads 21 may pivot during the arcuate upward and downward movement of the upper and lower arms 12 and 13, respectively.

Preferably each of the pads 21 is removably secured to the respective shafts 22, so that they may be selectively removed for cleaning, sterilizing or replacement thereof.

As shown in FIG. 13, if desired the pads may be removably secured on the distal end of each respective arm 12 or 13 by the distal end having a peg formed thereon and extending outwardly therefrom. Each pad 21 has an opening formed therein for snugly receiving one of the pegs therein. In this fashion, the pads 21 may be selectively removed from the pegs (shafts 22) for changing and or cleaning. This feature further permits the use of pads 21 of varying sizes, shapes, thicknesses and composition.

Figures 14, 15:
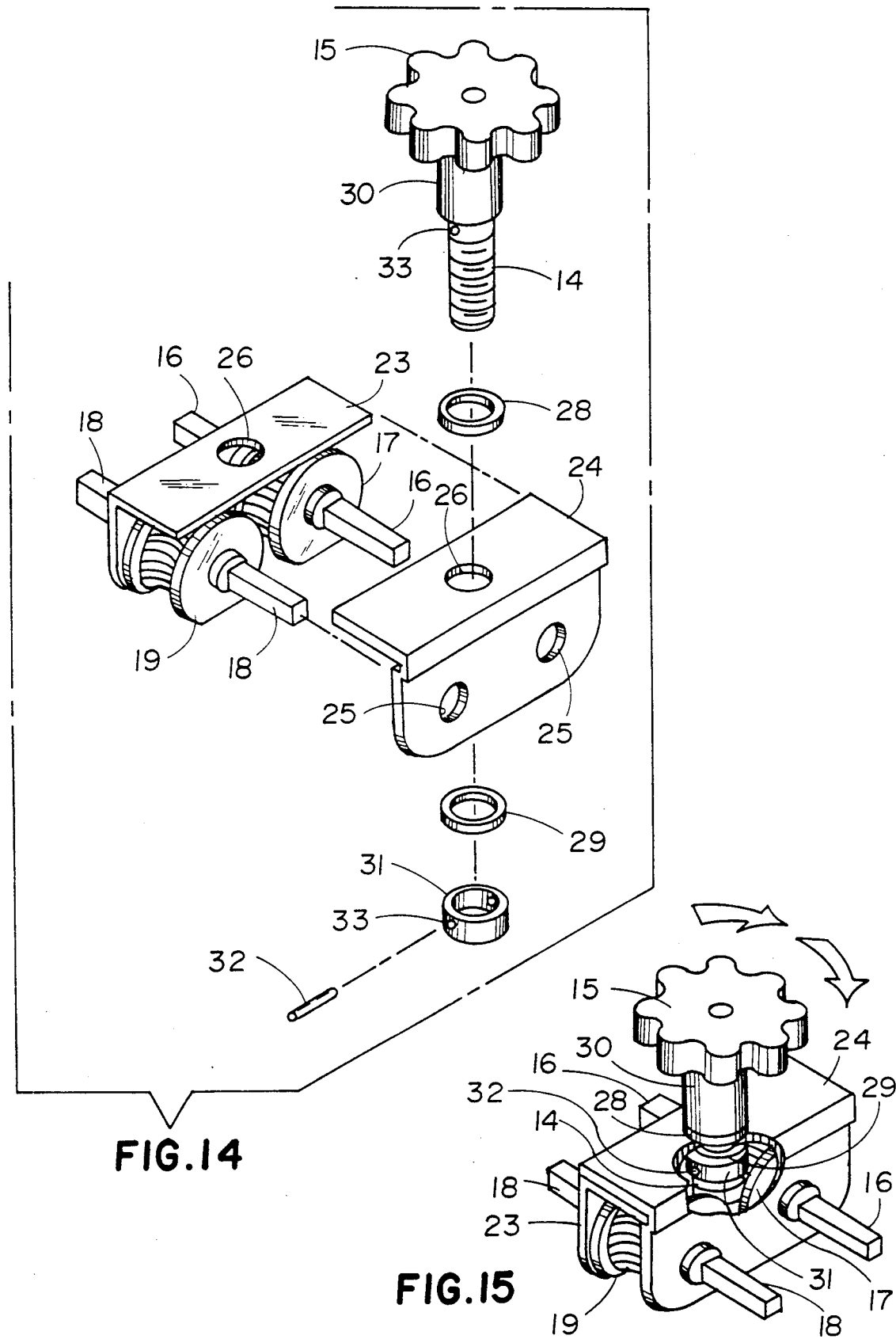
FIG. 14 is a perspective view of the first "L" shaped section of the housing with the upper and lower worm wheel shaft journaled in the openings and showing the opening on the "L" shaped section.
FIG. 15 is a perspective view of the device with a portion cut away to show the worm being threaded into the housing with the sleeve and pin to secure the worm therein.
Figures 16A, 16B:
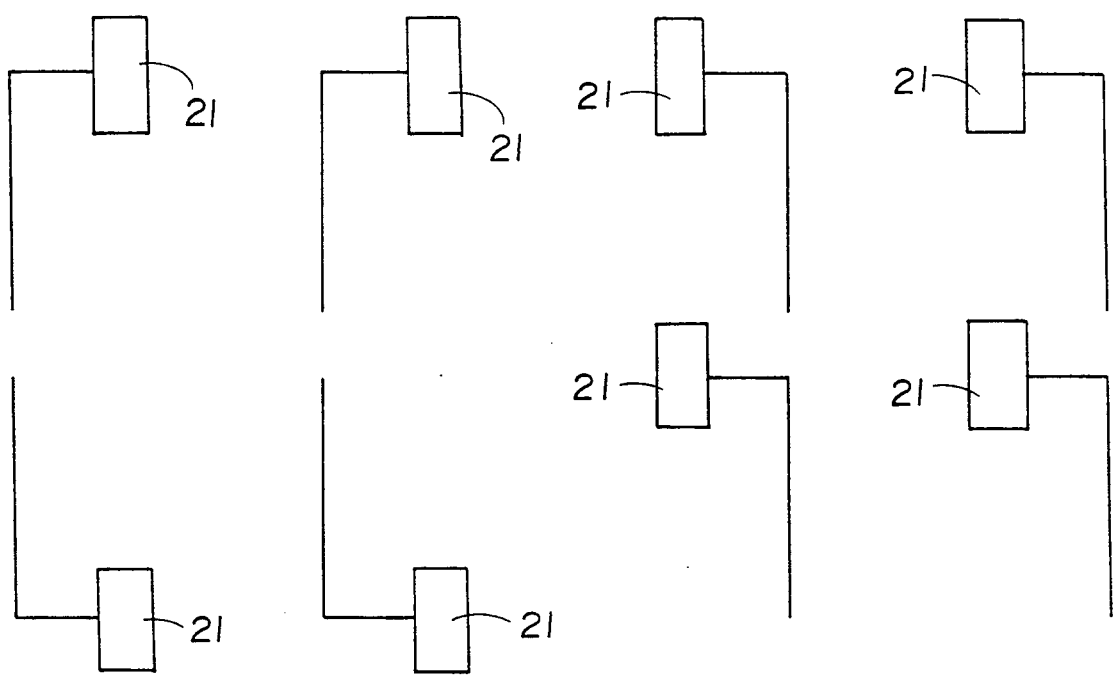
FIGS. 16A-D are diagramatic views of alternate arrangements of the pads on the distal ends of the arms showing inwardly, outwardly and combination extension of the pads.
Figures 16C, 16D:
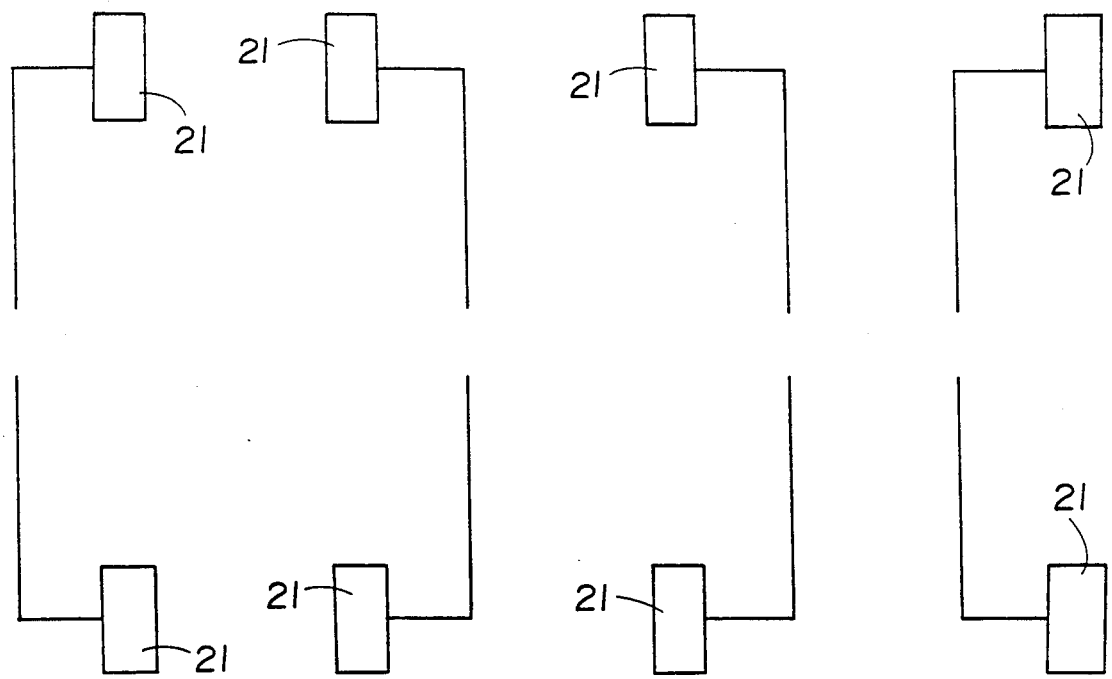

FIGS. 14–15 illustrate the assembly of the device. The housing 11 comprises a first, inner "L" shaped section (side portion) 23 and a second, outer "L" shaped section (side portion) 24 nested to form a "U" shaped channel having a pair of legs and a base. Each of the legs of the "U" shaped channel has aligned upper and lower circular openings 25. The upper worm wheel shaft 16 and the lower worm wheel shaft 18 are journaled through these openings 25. The base of the "U" shaped channel has a midpoint and a circular opening 26 at the midpoint of each section. The worm 14 may be inserted in this opening 26 with the knob 15 associated with the worm 14 extending outwardly from the housing 11.

In a preferred embodiment, the worm 14 has an associated shoulder 30 which is integral with the worm 14. When assembled, the shoulder 30 is disposed outwardly from the housing 11 with the edge of the shoulder adjacent to outer section 24 of the housing 11 and a washer 24 therebetween. The knob 15 is secured to the shoulder 30. The worm 14 extends inwardly from the housing 11 and has a transverse opening 33 bored therethrough adjacent to the inner section 23 of the housing 11. The worm 14 is inserted in a sleeve 31 which has a tranverse opening 33 bored therethrough such that the opening 33 in the sleeve 31 communicates with the opening 33 in the worm 14. A pin 32 is inserted through the opening 33 in the sleeve 31 and the opening 33 in the worm 14. When the pin 32 is so inserted (press-fitted), the worm 14 and the shoulder 30 are secured against the inner and outer sections 23 and 24, respectively of the housing 11 and longitudinal movement of the worm 14 is prevented. A washer 28 is disposed between the shoulder 30 and the outer section 24 and another washer is disposed between the sleeve 31 and the inner section 23. Preferably, the washer is fabricated of nylon or teflon. Rotation of the knob 15 produces rotation of the worm 14 about its longitudinal axis in opening and closing directions.

Each worm wheel 17, 19 has a flat side thereon. When these flat sides are aligned, as for example on a flat surface, and the worm 14 threaded therebetween, the worm wheels 17, 19 are cooperatively associated with the worm 14 for synchronized rotation. In this manner, rotation of the worm 14 in a first opening direction rotates each of the worm wheels 17, 19 in the respective first opening direction simultaneously. Rotation of the worm 14 in a second closing direction rotates each of the worm wheels 17, 19 in the respective second closing direction simultaneously.

FIGS. 16A–D show the versatility of the device in numerous arrangements of the pads 21 on the upper arms 12 and the lower arms 13 so that the device may be adjusted for the individual jaw. The distal ends of the arms have a peg 22 formed thereon. The pads 21 are carried on these pegs 22. Slidably mounting the proximal ends of the arms 12, 13 on the shaft 16, 18 permits selection of inward or outward extension of the pegs 22 on the distal end of the arms. Thus, it is possible to have any combination of inward and outward positioning of the pegs 22 (and the associated pads 21) on the upper and lower arms 12, 13. It is possible to have all pads 21 facing inwardly, all facing outwardly, or some inward and some outward as required for the specific needs of the patient. Thus, numerous combinations not illustrated in FIG. 16 can be obtained. Furthermore, the arm positioning, the pad 21 positioning and the pad thickness may be adjusted to accommodate missing teeth or other irregularities within the mouth. In all instances, the reference to contact of the device to the jaw (the mandible or lower jaw, or the maxilla or upper jaw) may also mean contact with the teeth or gums of the patient.

A stop may be placed on the device to limit the extent of opening of the distal ends of the arms 12, 13. In the case of human jaw, this may be for 60 mm of opening.

Obviously many modifications can be made of the device without departing from the basic spirit of the invention. For example, if desired only one upper and one lower arm may be provided. Accordingly, it will be appreciated by those skilled in the art the within the scope of the appended claims, the invention may be practiced other than has been specifically described herein.

What is claimed is:

1. In a device intended to be inserted into a patient's mouth for treating a patient suffering from trismus or other related medical or dental problems, wherein the device includes at least one articulatable arm having a distal end means provided with a laterally-projecting pin, the pin having an end extending outwardly from said arm, the improvement which comprises a removable pad for the distal end means of the arm, the pad being formed of a pliable material and having a bore formed therein for cooperation with the pin, wherein the pad may be slidably received on the end of the laterally-projecting pin on the arm, pivotably mounted thereon and freely rotatable without restriction about the pin, whereby the pad may be slidably removed from the arm, and whereby a replacement pad may be disposed thereon following treatment of the patient with the device.

2. In a device intended to be inserted into a patient's mount for treating a patient suffering from trismus or other related medical or dental problems, wherein the device includes at least one articulatable arm having a distal end means provided with a laterally-projecting pin, the improvement which comprises a pad for the distal end means of the arm, the pad being substantially oblong, and the pad having a bore formed therein, wherein the pad may be slidably received on the laterally-projecting pin on the arm, such that the pad is pivotably mounted on the arm, and wherein the pad is removed from the arm following treatment of the patient with the device, wherein the pad has a length and a width, the length being greater than the width, the bore in the pad being disposed in the length of the pad and parallel to the width of the pad.

3. The device of claim 2, wherein the bore in the pad extends transversely through the pad.

4. In a device intended to be inserted into a patient's mouth for treating a patient suffering from trismus or other related medical or dental problems, wherein the device includes at least one articulatable arm having a distal end means provided with a laterally-projecting pin, the improvement which comprises a pad for the distal end means of the arm, the pad being substantially oblong, and the pad having a bore formed therein, wherein the pad may be slidably received on the laterally-projecting pin on the arm, such that the pad is pivotably mounted on the arm, and wherein the pad is removed from the arm following treatment of the patient with the device; wherein the pad is formed from a pliable material.

5. In a device intended to be inserted into a patient's mouth for treating a patient suffering from trismus or other related medical or dental problems, wherein the device includes at least one articulatable arm having a distal end means provided with a laterally-projecting pin, the pin having an end extending outwardly from said arm, the improvement which comprises a pad for the distal end means of the arm, the pad being substantially oblong, and the pad having a bore formed therein, wherein the bore in the pad may be slidably received on the end of the laterally-projecting pin on the arm, such that the pad is pivotably mounted on the arm, and wherein the pad is removed from the arm and a replacement pad may be disposed thereon following treatment of the patient with the device; the pad having a length and a width, the length being greater than the width, the bore in the pad being disposed in the length of the pad and parallel to the width of the pad, the bore extending transversely through the pad; and wherein the pad is formed from a pliable material.

6. In a device intended to be inserted into a patient's mouth for treating a patient suffering from trismus or other related medical or dental problems, wherein the device includes at least one articulatable arm having a distal end means, the improvement which comprises a pad for the distal end means of said arm, the pad being formed of a non-metallic material, and means for pivotably mounting the pad on said arm, whereby the pad is slidably removable from said arm without the use of tools, and whereby a replacement pad may be disposed on the arm following treatment of the patient with the device.

* * * * *